United States Patent
Krutmann et al.

(10) Patent No.: US 8,765,691 B2
(45) Date of Patent: Jul. 1, 2014

(54) OSMOLYTES FOR THE TREATMENT OF ALLERGIC OR VIRAL RESPIRATORY DISEASES

(75) Inventors: Jean Krutmann, Wegberg (DE); Georg Lentzen, Herdecke (DE); Thomas Schwarz, Heilbronn (DE)

(73) Assignee: Bitop AG (DE)

( * ) Notice: Subject to any disclaimer, the term of this patent is extended or adjusted under 35 U.S.C. 154(b) by 933 days.

(21) Appl. No.: 12/675,264

(22) PCT Filed: Aug. 25, 2008

(86) PCT No.: PCT/EP2008/006959
§ 371 (c)(1),
(2), (4) Date: Oct. 5, 2010

(87) PCT Pub. No.: WO2009/027069
PCT Pub. Date: Mar. 5, 2009

(65) Prior Publication Data
US 2011/0053896 A1    Mar. 3, 2011

(30) Foreign Application Priority Data

Aug. 27, 2007 (DE) .................. 10 2007 040 615

(51) Int. Cl.
*A61K 31/185* (2006.01)
*A61K 31/205* (2006.01)
*A61K 31/505* (2006.01)
*A61K 31/66* (2006.01)

(52) U.S. Cl.
USPC ............. 514/25; 514/129; 514/171; 514/256; 544/235; 558/171

(58) Field of Classification Search
USPC ............... 514/25, 129, 171, 256; 544/235; 558/171
See application file for complete search history.

(56) References Cited

U.S. PATENT DOCUMENTS

| | | | | |
|---|---|---|---|---|
| 4,871,545 A | * | 10/1989 | Dethlefsen | 424/470 |
| 5,876,780 A | * | 3/1999 | Virtanen et al. | 426/623 |
| 5,880,098 A | | 3/1999 | Haussinger | |
| 6,602,514 B1 | * | 8/2003 | Bunger et al. | 424/401 |
| 7,147,849 B2 | * | 12/2006 | Barth | 424/130.1 |
| 2001/0056068 A1 | * | 12/2001 | Chwalisz et al. | 514/21 |
| 2002/0151541 A1 | * | 10/2002 | Pairet et al. | 514/217.05 |
| 2003/0147937 A1 | * | 8/2003 | Schwarz | 424/439 |
| 2004/0028631 A1 | | 2/2004 | Schwarz | |
| 2004/0071691 A1 | * | 4/2004 | Barth | 424/130.1 |
| 2004/0115236 A1 | * | 6/2004 | Chan et al. | 424/423 |
| 2006/0246007 A1 | | 11/2006 | Krutmann | |
| 2007/0122464 A1 | | 5/2007 | Krutmann | |
| 2008/0014153 A1 | | 1/2008 | Schwarz | |
| 2009/0060876 A1 | | 3/2009 | Schwarz | |
| 2010/0048900 A1 | | 2/2010 | Schwarz | |
| 2011/0152294 A1 | | 6/2011 | Krutmann | |

FOREIGN PATENT DOCUMENTS

| | | | | |
|---|---|---|---|---|
| EP | 0816509 A2 | * | 1/1988 | C12P 19/44 |
| WO | WO 92/17170 A1 | * | 10/1992 | A61K 31/185 |

OTHER PUBLICATIONS

The Merck Manual, 1992, pp. 189-197.*
Volkov, V.T. Tubercle and Lung Disease, Oct. 1995, 76(1), p. 59.*
Shima et al, Arch. Microbiol. 1998, 170, 469-72.*
Buommino et al, Cell Stress & Chaperones, 2005, 10(3), 197-203.*
Gennaro, A.R. Remington: The science and Practice of Pharmacy, 2000, pp. 721, 725, 729.*

* cited by examiner

*Primary Examiner* — Ganapathy Krishnan
(74) *Attorney, Agent, or Firm* — Berliner & Associates

(57) ABSTRACT

The present invention relates to the use of osmolytes for treating allergic or viral respiratory diseases, e.g. allergic rhinitis (hay fever) as well as rhinovirus and/or adenovirus infections. The invention also relates to a medicament preparation containing one or more compounds from the group of osmolytes. The group of osmolytes used in the invention comprises various low-molecular substances, more specifically ectoine, 4,5,6,7-tetrahydro-2-methyl-1H-[1,3]-diazepine-4-S-carboxylic acid (homoectoine), hydroxyectoine, di-myo-inositol-phosphate (DIP), to cyclic 2,3-diphosphoglycerate (cDPG), 1,1-diglycerol phosphate (DGP), β-mannosylglycerate (firoin), β-mannosylglyceramide (firoin-A), dimannosyl-diinositol phosphate (DMIP), glucosylglycerol, taurine, betaine, citrulline, and/or a derivative, e.g. an acid, salt, or ester of said compounds.

15 Claims, 1 Drawing Sheet

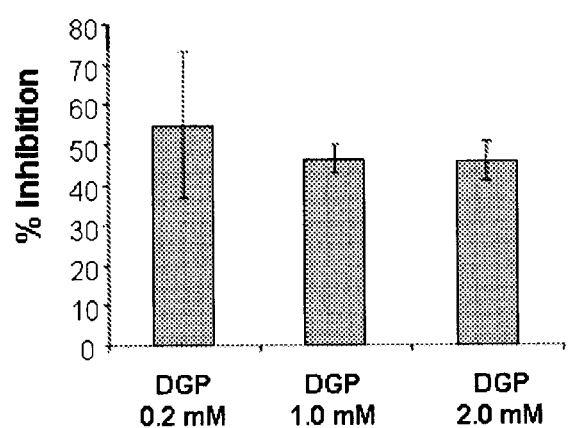

OSMOLYTES FOR THE TREATMENT OF ALLERGIC OR VIRAL RESPIRATORY DISEASES

Osmolytes originating from extremophilic microorganisms form a known group of low-molecular protective substances. Extremophiles are very extraordinary microorganisms in that they grow optimally under extreme conditions, e.g. in the presence of high salt concentrations (up to 200 g NaCl/l) and at high temperatures (60-110° C.). In mesophilic ("normal") organisms, such conditions is would cause massive damage to cell structures. For this reason, much research was done in the last several years with a view to identifying the biochemical components that bring about the remarkable thermal, chemical and physical stabilization of the cell structures. While many enzymes from hyperthermophilic microorganisms are also stable at high temperatures, this does not generally apply to the cellular structures of thermophilic and hyperthermophilic organisms. The high temperature stability of cell structures is caused, in a large measure, by low-molecular organic substances (compatible solutes, osmolytes) in an intracellular medium. During the last few years, several new types of osmolytes were identified, for the first time, in extremophilic microorganisms. In some cases, the role that these compounds play in the protection of cellular structures from heat and dryness has already been demonstrated (Lippert, K., Galinski, E. A. (1994), *Appl. Microbiol. Biotech.* 37, 61-65; Louis, P., Trüper, Galinski, E. A. (1994), *Appl. Microbiol. Biotech.* 41, 684-688; Ramos, Raven, Sharp, Bartolucci, Rossi, Cannio, Lebbink, v. d. Oost, de Vos, Santos (1997), *Appl. Environm. Microbiol.* 63, 4020-4025; Da Costa, Santos, Galinski (1998), *Adv. In Biochemical Engineering Biotechnology,* 61, 117-153).

The osmolytes found in extremophilic microorganisms (compatible solutes) are not formed by human or animal cells.

Viral Respiratory Diseases

Rhinoviruses are infective agents that cause coryza, also known as common cold. They belong to the picornaviridae (name derived from pico=small and RNA) family of viruses. Within this family, they form the *rhinovirus* genus. 117 serotypes are known today.

Rhinoviruses infect the mucous membranes of the nasal and pharynx cavities, they remain strictly localized and do not cause a generalized infection. A common cold develops. In rare cases, children may get bronchitis. The human body reacts to the virus attack with an inflammation reaction of the nasal mucosa. The mucosa vessels become more penetrable, liquid can exit, and the nose starts to run. At a later stage, the nasal mucosa swells up to a thickness of a half centimeter, making it almost impossible to breathe through the nose. Other symptoms may develop as well, such as malaise and headache. Besides the viral infection proper, a secondary infection may often occur due to bacteria in the throat and the pharynx cavities.

Human adenoviruses are viruses of the adenoviridae family. Viruses of this family infect both humans and animals. They were first isolated in human adenoids, from which the name of these viruses is derived.

Adenoviruses cause mainly respiratory diseases. Depending on the serotype involved, however, a number of other diseases may also develop, such as gastroenteritis, conjunctivitis, cystitis, rhinitis, pharyngitis or diarrhea. The symptoms of the adenovirus-induced respiratory disease range from the common cold to bronchitis and pneumonia. Patients with a weakened immune system have an increased risk for developing serious complications of the adenovirus infections, such as ARDS or Acute Respiratory Distress Syndrome.

Allergic Respiratory Disease

The number of allergic diseases is rapidly rising worldwide. Studies have shown that a worldwide average of 7.5% of children and youths suffer from rhinoconjunctivitis (hay fever of an allergic nature, combined with eye symptoms) (Worldwide variation in prevalence of symptoms of asthma, allergic rhinoconjunctivitis and atopic eczema: ISAAC, Lancet, 351, 1225-1332, 1998). Despite intensive research efforts, the pathogenesis of rhinoconjunctivitis is still not fully known. Although significant progress has been achieved in the medicament treatment of this disease during the last few years, the therapy is still unsatisfactory. The acute symptoms (itching, irritation, swelling, runny nose and/or watery eyes) of rhinoconjunctivitis can be effectively controlled by antihistamines, among others. However, they have hardly any therapeutically relevant effect on the continuously progressing inflammation underlying the disease. That inflammation is a defense reaction of the organism and its tissue against damaging irritation, which reaction aims to repair the damage or at least restrict it locally and eliminate its cause (e.g. invading bacteria or foreign bodies). The inflammation may be triggered by microorganisms (bacteria, viruses, fungi or parasites), foreign bodies (pollen, asbestos or silicate crystals), tissue destruction due to mechanical damage, chemical noxes and physical effects as well as body-related causes (collapsing tumor cells, extravasal blood, autoimmune reactions) or crystals of substances precipitated in the body (uric acid, calcium oxalate and calcium phosphate, cholesterol). Due to the action of the noxes and with the aid of the T helper cells, inflammation mediators are released in the body, especially histamine along with interleukin-8, leukotrienes and tumor necrosis factor-alpha (TNF-alpha), which activate the subsequent inflammation defense cascade in the body. The strain produced by the afore-mentioned noxes has also an impact on the adhesion molecules of the epithelia affected by the external influence. Under the action of the noxes, these molecules are produced more or less abundantly—either directly or through the body reaction. The ICAM-1 molecule, for example, is expressed more strongly in the affected cells as a result of the strain.

Allergic Rhinitis and Asthma

Allergens contained in the inhaled air cause reactions in the respiratory tract, which are typically associated with mucosa edema and hypersecretion (allergic rhinitis, hay fever) as well as bronchospasm (asthma). Food allergens, in contrast, cause primarily stomach and intestinal symptoms, such as nausea, vomiting and diarrhea. The skin reacts to allergens with itching, swelling and urticaria as well as atopic dermatitis (neurodermatitis). However, if the allergen is introduced directly into the blood system (e.g. through infusion of blood products, medicaments) or if allergen exposure is extraordinarily severe, a systemic instantaneous reaction will develop, which, under certain circumstances, may lead to a life-threatening blood pressure drop (anaphylactic shock). The effects of osmolytes (notably ectoine) in the treatment of atopic dermatitis and inflammations of the stomach and intestinal tract have been described in the German Patent Application DE 103 30 243.3 (osmolytes for the treatment of neurodermatitis) and the German Patent Application DE 10 2005 011 442.3 (compositions comprising compatible solutes for oral application) and are know from the prior art.

Acute and/or chronic inflammations of the main nasal cavity and/or the paranasal sinuses are mainly treated with deswelling nose sprays, cortisone-containing nose sprays, mucolytic substances or antibiotics. All named substances cause side effects. Cortisone-containing nose sprays often trigger allergic reactions by themselves.

Very often, allergic rhinitis (rhinoconjunctivitis) is regarded as a petty disease by both the patient and the physician and is therefore treated inappropriately. Later on, however, the disease may spread to the lower airways, i.e. the relatively harmless rhinitis may turn into asthma bronchiale, a disease which must be taken very seriously. For this reason, it is indispensable that even the allergic rhinoconjunctivitis be treated appropriately and intensively or that preventive treatment be provided. Only then can patients live symptom-free and only then can the disease be prevented from developing into what may be a life-threatening condition.

At the present time, corticosteroids are the most effective substances for treating the inflammation underlying rhinoconjunctivitis. However, given the potential systemic side effects of these substances, many patients and even some physicians do not use these medicaments or do so only reluctantly or only in an advanced phase of the disease.

Antihistamines are used in the acute phase of rhinoconjunctivitis allergica for relieving the often painful symptoms. However, despite the development of new antihistamines, the systemic administration of these substances has some sedating side effects (inability to drive, fatigue), which may vary with the individual user. These side effects significantly restrict the use of antihistamines. While it is true that the new generation of preparations has substantially less side effects, their effectiveness is in many cases considerably reduced.

BRIEF DESCRIPTION OF THE DRAWINGS

Reference is made to the following descriptions taken in conjunction with the accompanying drawing, in which:

FIG. 1 is a graph showing inhibition of ICAM-1 expression by DGP for various application concentrations.

DETAILED DESCRIPTION

Surprisingly, it was discovered that the use of osmolytes, such as ectoine, is advantageous—in a nasally applicable form, for example—in the prophylaxis and treatment of "rhinitis allergica (hay fever)". The rationale behind this is based on the observation that, as part of the inflammation reaction, which is typical of rhinitis allergica (hay fever), upregulation of adhesion molecules, such as ICAM-1, takes place in the nasal epithelial cells due to interaction of these cells and the relevant allergens (e.g. pollen), which is the basis for the development of the clinical symptoms of the common cold. The inventors observed that ICAM-1 upregulation caused by pro-inflammatory stimuli can be inhibited by ectoine. Thus, an osmolyte-containing, nasally applicable preparation can be used in the treatment and prophylaxis of hay fever. Owing to the exclusively water-structure-altering physical effect of osmolytes, virtually none of the typical steroid-specific side effects may be expected.

Surprisingly, the second indication treatable with ectoine is the use of osmolytes in the prophylaxis of rhinovirus and/or adenovirus infections of the respiratory tract. Virus infections, especially rhinovirus infections, are a main cause of the exacerbation of asthma. It has been known for years that the ICAM-1 molecule functions not only as adhesion molecule for other cells, but is also a receptor for rhinoviruses (common cold viruses). Moreover, the rhinovirus infection triggers increased ICAM-1 expression in respiratory epithelia. On this basis, osmolyte treatment can prevent or reduce upregulation of ICAM-1 molecules in the nasal epithelium and thus expression of this rhinovirus receptor, so that the development and onset of a rhinovirus infection in humans can be prevented or reduced. Within the adhesion complex of the cells, there is the CAR receptor, which is used as a docking site for adenoviruses. The various serotypes of the adenoviridae then use further different receptors (integrins, CD46, heparan sulfate glucosamine-glycans, CD80, CD86) and members of MHC-1 in order to penetrate into the cells. The change in expression of adhesion molecules brought about by osmolyte treatment can thus also reduce or even prevent the potential of adenoviruses to dock onto, or penetrate into, the cell.

Surprisingly enough, it was further found that topical application, effected with the help of nasal sprays, to the nasal epithelia is advantageous for various reasons. Application may be effected simultaneously, sequentially or separately. Topical application of the osmolyte-containing nose spray quickly eliminates the acute symptoms (e.g. irritation, itching, swelling) without causing any side effects. The osmolytes contained in the preparation make it possible to successfully treat the inflammations underlying the disease. In borderline cases, the treating doctor often cannot determine with certainty whether the disease is "only" a rhinoconjunctivitis or a respiratory disease, such as asthma bronchiale. An advantageous aspect of the combination according to the invention is the fact that it can be used also to treat diseases of the lower and upper respiratory tract.

Surprisingly, it has further been found that the side effects of nose sprays containing the active substances (including, but not limited to, glucocorticoids, antihistamines) can be significantly reduced by the addition of osmolytes. Here, the osmolytes can be used in combination with other active principles, thus lowering the necessary concentration of the other substance. Another option would be using preventive administration of osmolytes, which can straightaway reduce the side effect profile of the substances to be administered later. This makes the general combination of extremolytes and steroids an attractive approach. Using a combination therapy comprising osmolytes (especially ectoine and hydroxyectoine) and other intranasally or intraocularly applied active substances that could produce undesirable side effects is thus an attractive option as well. Another imaginable approach is to admix to osmolytes active substance formulations which are administered nasally or ocularly for the purpose of treating an organic disease (e.g. cancer), but which have an inflammatory side effect on the nasal epithelium. Joint administration of osmolytes and, e.g. glucocorticoids or antihistamines, or preventive administration of osmolytes, given prior to starting a therapy with these substances, could generally be used, in many forms of application (topical, dermal, intraperitoneal, intravenous, intramuscular, oral), as an effective method to lessen the side effects of the substances or to lower the application concentrations of the active substances by combining the active principles of osmolytes with those of the active substances that are administered simultaneously or at a later time, which would relieve the strain on the patient treated.

The compatible solutes (osmolytes) to be preferably used are ectoine, 4,5,6,7-tetrahydro-2-methyl-1H[1,3]-diazepine-4-S-carboxylic acid (homoectoine), hydroxyectoine, di-myo-inositol-phosphate (DIP), cyclic 2,3-diphosphoglycerate (cDPG), 1,1-diglycerol phosphate (DGP), 6-mannosylglycerate (firoin), 6-mannosylglyceramide (firoin-A), dimannosyl-diinositol phosphate (DMIP), glucosylglycerol, taurine, betaine, citrulline, and/or derivatives of these compounds such as salts, esters or acids. The concentrations of the compatible solutes are typically between 0.01 and 20% w/w, preferably between 0.1 and 10% w/w, especially preferably between 0.1 and 5% w/w, related to their total weight.

By adjusting osmolyte administration to the respective treatment, application and indication, it is possible to obtain the effective concentrations even with low dosages. The administration of osmolytes permits to lessen the irksome reactions, such as itching, runny nose, and prevents the inflammation from progressing. Thus better patient compliance may be expected.

Intranasal or intraocular administration, in particular, produces not only a quick effect, but ensures also high therapeutic efficacy along with a strong anti-inflammatory effect. Thus the object of the present invention is to make available means for the prevention or therapy of immunological oversensitive reactions, notably those associated with allergic rhinitis, and for the prevention of rhinovirus and/or adenovirus infections. Such means provide a broader (deliberately non-mono-specific) therapeutic approach that is low in side effects and thus more effective. One aspect of the present invention relates to the use of osmolytes for the production of a medicament or medicinal product, e.g. in the form of a nose spray or in the form of eye drops for the prevention or therapy of allergic rhinitis and virus infections, which—due to the osmolyte-induced protection of nose epithelial cells—reduces expression of pro-inflammatory gene products (e.g. ICAM-1) which are produced during inflammatory reactions.

The dosage can be divided into several doses per day, the single dose being governed by the osmolyte used and, in particular, by the general condition of the patient (age, weight, etc.) and the severity of the disease.

For topical application, several different pharmaceutical formulations, e.g. nose spray, nose and eye drops, are suitable. Owing to the water-soluble property of the osmolyte (preferably ectoine), formulations with these active substances can preferably be designed as aqueous solutions.

In addition to the effective osmolytes, the pharmaceutical preparations according to the invention may contain further ingredients, such as preservatives, stabilizers, isotonizing agents, thickeners, suspension stabilizers, pH adjusting agents, buffer systems and surfactants. Moreover, the pharmaceutical preparations according to the invention may contain further active substances, such as antihistamines or steroid substances (e.g. loteprednol etabonate).

The following substances can be used as preservatives: benzalkonium chloride, chlorobutanol, thiomersal, methyl paraben, propyl paraben, sorbic acid and its salts, sodium edetat, phenylethyl alcohol, chlorhexidine hydrochloride/acetate/digluconate, cetylpyridinium chloride/bromide, chlorocresole, phenylmercury acetate, phenylmercury nitrate, phenylmercury borate, phenoxyethanol.

Suitable auxiliary substances for isotonizing the formulations are, for example, sodium chloride, potassium chloride, mannitol, glucose, sorbitol, glycerol, propylene glycol. As a general rule, these agents are used in concentrations of between 0.1 to 10%.

The formulations covered by the invention may also contain suitable buffer systems or other auxiliary substances for adjusting and maintaining the pH value in the range of 4 to 8, preferably 5 to 7.5. Suitable buffer systems are citrate, phosphate, tromethamol, glycine, borate, acetate. These buffer systems can be produced using such substances as citric acid, monosodium phosphate, disodium phosphate, glycine, boric acid, sodium tetraborate, acetic acid or sodium acetate.

Further auxiliary substances that can be used for adjusting the pH value are hydrochloric acid or sodium hydroxide. Substances which can serve as surfactants for the formulations are benzalkonium chloride, cetylpyridinium chloride, tyloxapol, various polysorbates [Tween™] as well as further polyoxyethylated substances and poloxamers.

The following example of a nose spray serves to illustrate the invention without restricting it.

Nose Spray Containing Ectoine (0.1%)

Pour approx. 45 kg of purified water into a suitable agitating vessel. Add, one by one, the active substance (ectoine), hydroxypropyl methylcellulose, sodium acetate, benzalkonium chloride and sorbitol solution and dissolve them by agitating. Using purified water, fill up the solution obtained to a volume of 49.5 liters. Adjust the pH value of the solution with 1 N sodium solution to a pH of 6.0. Fill up to a final volume of 50.0 with purified water and agitate. After passing the solution through a suitable filter, fill it into bottles which are to be provided with an appropriate nose spray pump.

Effectiveness Studies

Example 1

Sensitizing Treatment and Induction of Allergic Reactions in Mice Using Ovalbumin (OVA)

Seven-months-old mice of the inbred strain Balb/c were sensitized by injecting them intraperitoneally with a mixture of ovalbumin and aluminum hydroxide contained in a total volume of 200 µl buffer (PBS). The injection was made twice, once on day 0 and once on day 14. The size of each group tested was n=8.

In order to subsequently induce the allergic reaction in the lungs of the mice, i.e. to trigger the acute allergic asthma, the mice were treated inhalatively with an ovalbumin aerosol for 30 minutes each on days 28 and 38. For this purpose, the mice were placed in a plexiglass chamber, into which a misty 1% OVA solution was introduced through an inhaler.

Treatment of the Animals with Ectoine Solution or 0.9 Salt Solution

For ectoine treatment, the animals were anesthetized with a mixture of ketamine and rompune. 50 µl of a sterile ectoine solution or 0.9% salt solution was applied in front of the nostrils with glass capillaries until the solution was completed inhaled. The treatments—14 in all—started on day 0. The last treatment was administered on day 32.

Result

The end points of the study were defined as the bronchial hyperreactivity as measured with a plethysmograph, the bronchoalveolar lavage (BAL) cellular composition and the release of OVA-specific igE and igG1 antibodies.

A significant positive effect of the ectoine solution treatment, compared to the treatment with 0.9% salt solution, on these end points was observed.

Example 2

Sensitizing Treatment and Induction of Allergic Asthma in Rats Using Ovalbumin (OVA)

The study population consisted of 4 treatment groups, a reference group, a sham-sensitized and vehicle-treated negative control group, and a vehicle-treated positive control group. The group size was n=16.

In the first phase of the study, all animals, except for the sham-sensitized group, were systemically sensitized to ovalbumin (OVA) plus adjuvants, the negative control group was given NaCl. On days 7 and 14, the animals were intratracheally boosted with OVA (to enhance the sensitizing effect). 48 h, 24 h and 2 h before the final inhalative allergen exposure was performed, three groups and a positive control group were subjected to an intratracheal pretreatment with the test substance, ectoine, at three dosage levels. The two control groups were given only NaCl. After expiry of the waiting period, the animals were anesthetized, orotracheally intubated in a gentle manner and—after placement of an oesophagus catheter and allowing the mice to reach a steady state—their lung functions (including such parameters as tidal volume, breathing frequency, dynamic compliance and lung resistance) were measured body-plethysmographically prior to provocation. The data was collected and evaluated using a computer program (HEM, Notocord/France) specifically developed for these lung function tests. Subsequently the defined inhalative exposure of the test animals to the allergen, ovalbumin, (ovalbumin challenge, model of an allergically induced asthmatic reaction) was performed.

Effect of the Ectoine Solution on the Early Allergic Reaction

The lung function parameters were continuously recorded during and after exposure in order to measure bronchospasm.

A significant positive effect of the ectoine solution on lung function parameters was found in comparison to the negative control.

Effect of the Ectoine Solution on the Late Allergic Reaction

The late allergic phase was tested 24 h after the ovalbumin challenge. First the animals were tested for airway hyperreactivity to unspecific stimuli. For this purpose, a hyperreactivity test was made in the form of a progressively increasing inhalative acetyl-choline provocation. Then the animals were killed painlessly and their lungs were lavaged (BAL). Using the lavage liquid, the total and the differential cell counts were determined including the number of esinophiles in the BAL.

Compared to the treatment administered to the negative control group, a to positive effect of the ectoine solution treatment on the late allergic reaction was clearly identified.

Example 3

Effect of Ectoine Nose Spray on the Allergic Reaction in Humans

The effect of an ectoine nose spray on the reaction occurring after an allergen challenge was tested in a randomized, double-blind crossover study involving 20 patients affected by allergic rhinitis.

At the start of the study, the patients were intranasally excited with a defined allergen and their allergic reaction was measured using various parameters. Subsequently, a two-week treatment with ectoine nose spray or a placebo nose spray (0.9% NaCl) was performed and a new excitation test with the defined allergen was made, after which the allergic reaction was measured again.

Following an appropriate washout phase, the patients were analogously treated with ectoine nose spray or a placebo nose spray in a crossover design.

This procedure made it possible to compare, intra-individually and inter-individually, the effect of the ectoine nose spray with that of the placebo solution. It was demonstrated in this study that the ectoine nose spray, in comparison to the placebo nose spray, brought about a significant improvement in allergic rhinitis.

Example 4

Reduction of ICAM-1 Expression by DGP

Human ceratinozytes were pretreated with DGP for 24 hours. After radiation using UVA rays (environment noxes) the quantity of ICAM-1 was measured. DGP was found to inhibit expression by 49% (see FIG. 1).

Example 5

Inhibition of ICAM-1 Expression by Ectoine

ICAM-1 expression was measured using differential reverse transcriptase-PCR (RT-PCR) and the Applied Biosystem Kit. To take account of the normal variations in the gene expression of skin cells, ICAM-1 expression is put into relationship to the constitutively formed house-keeping gene, β-actin. The semi-quantitive analysis of RT-PCR was performed by ion exchange chromatography using a UV spectrophotometer (A260). (A) Non-pretreated, radiated control sample (B) pre-incubated for 24 h with 1 mM RonaCare™ Ectoin and radiated with a single dose of 30 J/cm$^2$ or (C) pre-incubated for 24 h with 1 mM ectoine, non-irradiated. UVA radiation induces upregulation of ICAM-1 expression. Pretreating the ceratinzytes with 1 mM ectoine can, at all times, almost completely neutralize the ICAM-1 induction caused by UVA radiation.

The invention claimed is:

1. A method for treating an allergic or viral respiratory disease in an individual in need of such treatment, the method comprising treating an individual with a medicament comprising at least one compatible solute selected from the group consisting of ectoine, 4,5,6,7-tetrahydro-2-methyl-1H-[1,3]-diazepine-4-S-carboxylic acid (homo-ectoine), hydroxyectoine, glucosylglycerol, and salts or esters thereof,
    wherein the respiratory disease is rhinitis allergica, asthma, common cold, coryza, bronchitis, influenza or pneumonia.

2. The method according to claim 1, wherein the medicament further comprises at least one substance selected from the group consisting of antihistamine, steroid, mast cell stabilizer, leukotriene receptor modifier, and B2-sympathomimetic substance.

3. A method for treating acute or chronic inflammation reactions of the respiratory tract caused by substances belonging to the class of steroids in an individual in need of such treatment, the method comprising treating an individual with a medicament comprising at least one compatible solute selected from the group consisting of ectoine, 4,5,6,7-tetrahydro-2-methyl-1H-[1,3]-diazepine-4-S-carboxylic acid (homo-ectoine), hydroxyectoine, glucosylglycerol, and salts or esters thereof.

4. The method according to claim 3, wherein the compatible solute has a concentration of between 0.01 and 20% w/w relative to the total weight.

5. The method according to claim 4, wherein the compatible solute has a concentration of between 0.1 and 10% w/w relative to the total weight.

6. The method according to claim 5, wherein the compatible solute has a concentration of between 0.1 and 5% w/w relative to the total weight.

7. The method according to claim 3, wherein the medicament is available for application in liquid or semi-liquid form.

8. The method according to claim 3, wherein the medicament is available in the form of a spray, as eye drops or nose drops, or as an inhalable liquid or solid preparation.

9. The method according to claim 1, wherein the compatible solute has a concentration of between 0.01 and 20% w/w relative to the total weight.

10. The method according to claim 9, wherein the compatible solute has a concentration of between 0.1 and 10% w/w relative to the total weight.

11. The method according to claim 10, wherein the compatible solute has a concentration of between 0.1 and 5% w/w relative to the total weight.

12. The method according to claim 1, wherein the medicament is available for application in liquid or semi-liquid form.

13. The method according to claim 1, wherein the medicament is available in the form of a spray, as eye drops or nose drops, or as an inhalable liquid or solid.

14. The method of claim 1, wherein the respiratory disease is an allergic respiratory disease.

15. The method according to claim 14, wherein the medicament further comprises at least one substance selected from the group consisting of antihistamine, steroid, mast cell stabilizer, leukotriene receptor modifier, and B2-sympathomimetic substance.

* * * * *